(12) United States Patent
Forusz et al.

(10) Patent No.: US 6,436,446 B1
(45) Date of Patent: Aug. 20, 2002

(54) COMPOSITION FOR INCREASING BONE DENSITY

(75) Inventors: Samuel L. Forusz, Westlake Village, CA (US); Hanlan Liu, Pomona, NY (US); Rose M. Muatine, Burbank, CA (US)

(73) Assignee: Pharmavite LLC, Northridge, CA (US)

( * ) Notice: Subject to any disclaimer, the term of this patent is extended or adjusted under 35 U.S.C. 154(b) by 0 days.

(21) Appl. No.: 09/365,156

(22) Filed: Jul. 30, 1999

(51) Int. Cl.[7] ............... A61K 33/06; A61K 31/122; A61K 31/135; A61K 31/185; A61K 31/593; A61K 31/715; A61K 35/78; A61K 47/00; A23L 1/30; A23L 2/00

(52) U.S. Cl. ............... 424/682; 424/725; 424/757; 424/764; 424/773; 424/776; 426/72; 426/73; 426/74; 426/590; 426/654; 426/655; 426/658; 514/54; 514/60; 514/61; 514/167; 514/460; 514/553; 514/557; 514/682; 514/772; 514/777; 514/782; 514/783; 514/904; 514/905; 514/970

(58) Field of Search ............... 424/682, 195.1, 424/725, 757, 764, 773, 776; 426/72, 73, 74, 590, 654, 656, 658; 514/2, 54, 58, 60, 773, 777, 778, 782, 783, 904, 905, 970, 61, 167, 460, 553, 557, 682, 772, 403

(56) References Cited

U.S. PATENT DOCUMENTS

| | | | |
|---|---|---|---|
| 4,737,375 A | 4/1988 | Nakel et al. | 426/590 |
| 5,128,374 A | 7/1992 | Kochanowski | 514/574 |
| 5,389,387 A | 2/1995 | Zuniga et al. | 426/74 |
| 5,401,524 A | 3/1995 | Burkes et al. | 426/590 |
| 5,424,331 A | 6/1995 | Shlyankevich | 514/456 |
| 5,597,595 A | 1/1997 | DeWille et al. | 426/74 |
| 5,654,011 A | 8/1997 | Jackson et al. | 424/635 |
| 5,776,524 A | 7/1998 | Reinhart | 426/2 |
| 5,900,255 A * | 5/1999 | Ohta et al. | 424/602 |
| 6,150,399 A * | 11/2000 | Patel et al. | 514/456 |
| 6,171,633 B1 * | 1/2001 | Dulebohn et al. | 426/580 |

FOREIGN PATENT DOCUMENTS

| | | | |
|---|---|---|---|
| EP | 1 025 850 | * | 8/2000 |
| WO | 99/07392 | * | 2/1999 |

OTHER PUBLICATIONS

C. Coudray, et al., "Effect of Soluble or Partly Soluble Dietary Fibres Supplementation on Absorption and Balance of Calcium, Magnesium, iron and Zinc in Healthy Young Men," European Journal of Clinical Nutrition, Stockton Press 1997, pp. 375–380.

C. Lemort, et al., "Effect of Chicory Fructooligosaccharides on Ca Balance," Proc. of the Intern. Symposium, Dec. 4–5, 1997.

Hideo Tomomatsu, "Health Effects of Oligosaccharides," Food Technology, Oct. 1994, pp.61–65.

Orafti Active Food Ingredients, "Consumption a RAFTLINE® or RAFTILOS® Stimulates Calcium Abortion and Bone Mineral Density," Improvement of Calcium Absorption Nutritional File, pp. 1–9 (1998).

* cited by examiner

*Primary Examiner*—Jose' G. Dees
*Assistant Examiner*—Frank Choi
(74) *Attorney, Agent, or Firm*—Blakely, Sokoloff, Taylor & Zafman, LLP

(57) ABSTRACT

A method including administering a beverage composition suitable for human consumption including effective amounts of the following solubilized components, a calcium compound, an organic acid in an amount up to the equivalent amount of a calcium of the calcium compound, an isoflavone, and inulin wherein the effective amounts are sufficient to reduce the risk of bone density loss and are solubilized by a stabilizing agent including one or more of maltol, carrageenan and maltodextrin, and xanthan gum.

9 Claims, No Drawings

COMPOSITION FOR INCREASING BONE DENSITY

BACKGROUND OF THE INVENTION

1. Field of the Invention

The invention relates to nutritional supplements and more particularly to a composition and method for reducing the risks associated with bone density loss, e.g., the risks of osteoporosis.

2. Description of Related Art

Osteoporosis is a debilitating disease affecting as many as one in three women after menopause. The disease affects the skeletal structure making the skeletal structure weak and frail. Calcium and magnesium supplementation is seen as one way to protect against osteoporosis. Men also experience a loss in bone density with age. Accordingly, health care practitioners increasingly encourage calcium and magnesium supplementation for men and women of all ages.

In general, only about 30 percent of dietary calcium is absorbed by the body and deposited in the bone. Improved calcium (and magnesium) absorption in the body would have important consequences in the reduction of osteoporosis and bone fractures.

Several calcium and/or magnesium supplements have been introduced in recent years. U.S. Pat. No. 5,389,387 issued to Zuniga, et al. and U.S. Pat. No. 5,401,524 issued to Burkes, et al. describe a calcium beverage supplement composition. These compositions combine malic acid and citric acid with a calcium syrup such as calcium lactate. The malic acid and citric acid provide stability against precipitation of the calcium salt, as well as taste and mouth feel quality. U.S. Pat. No. 5,424,321 issued to Shlyankevich and U.S. Pat. No. 5,654,011 issued to Jackson, et al. describe beverage compositions including calcium, Vitamin D, magnesium, and zinc.

Soy isoflavones are another group of dietary acceptable compounds believed to be beneficial in the treatment and/or prevention of osteoporosis. U.S. Pat. No. 5,424,321 describes a composition for the treatment or prevention of osteoporosis that utilizes soy bean food products that contain natural phytoestrogens of the isoflavone or coumestan groups. The isoflavones include daidzein, genistein, and glycitein. The classes of isoflavones can also be derived synthetically. The patent claims that the soy isoflavones are effective in preventing osteoporosis by provoking an estrogenic response in post-menopausal women.

In general, it is believed that the majority of calcium and magnesium absorption occurs in the intestines. Certain oligosaccharides, including inulin, are believed to stimulate mineral absorption in humans. Oligosaccharides are also believed to increase the bifidobacteria population in the large intestine including the colon, contributing to beneficial effects in humans, including a reduction of harmful bacteria, toxic metabolites, and detrimental enzymes.

What is needed is a composition that improves the calcium and magnesium absorption in humans to increase bone density and reduce the risk of osteoporosis.

SUMMARY OF THE INVENTION

An improved supplement composition and a method of reducing bone density loss is disclosed. In one aspect, a composition suitable for human consumption combines a dietary acceptable amount of a calcium compound, a dietary acceptable amount of a magnesium compound, at least one soy isoflavone, inulin, and a dietary acceptable amount of Vitamin $D_3$. Other components, include but are not limited to, minerals such as phosphorus and zinc; vitamins including Vitamin C (ascorbic acid) and Vitamin K; stabilizing agents; acidifiers; and sweeteners.

The composition of the invention may be in the form of a ready to drink beverage, a beverage preparation of a dry mix or syrup concentrate, a wafer, a paste, or a bar. The composition may also contain a variety of levels of the individual components. For example, a desired daily amount of the individual components of the composition has been determined. This amount may be administered as a single dose or as several doses. Where the composition is a beverage, for example, the beverage may constitute, for example, one-eighth of a predetermined daily amount of the individual components, making the beverage suitable for consumption eight times daily as in the recommended daily amount of water intake.

In a beverage form, the invention maximizes the solubility of soy isoflavones in solution by, in one embodiment, including a stabilizing agent of at least one of maltol, a composition of carrageenan and maltodextrin, or xanthan gum. The beverage composition may be a clear or a colored solution without significant residue or sediment. The beverage is also, preferably, adjusted to a pH between 3 and 7 and more preferably between pH 4 and 5 at room temperature with an organic acid in an amount up to the equivalent amount of a calcium of the calcium compound.

As a method of reducing the risk of bone density loss, the invention contemplates the step of administering a composition suitable for human consumption comprising a portion of the daily predetermined amount of a calcium compound, a magnesium compound, an isoflavone, inulin, phosphorus, Vitamin $D_3$, Vitamin K, a zinc compound, and ascorbic acid. The composition may be administered in various forms, including as a beverage, a paste, or a bar. The amount of the individual components of the composition may be adjusted to provide a portion, including the entire portion, of a predetermined beneficial amount, such as a predetermined daily amount.

DETAILED DESCRIPTION OF THE INVENTION

The invention relates to a composition that includes a supplement to provide the dietary needs of individuals for nutrients to support adequate bone density and a healthy skeletal system. The composition also provides appropriate nutrients to reduce the risk of osteoporosis or to treat bone density loss associated with osteoporosis. The invention also relates to a method of reducing the risk of bone density loss commonly associated with the development or onset of osteoporosis.

In one embodiment, the composition of the invention comprises active ingredients of inulin, isoflavones such as soy isoflavones, minerals, and optionally one or more vitamins. More particularly, the composition includes, in one embodiment, a dietary acceptable amount of a calcium compound and a magnesium compound, together with a soy isoflavone, inulin, and a dietary acceptable amount of Vitamin $D_3$.

Calcium and magnesium are important in supporting a healthy skeleton system, by building bone mass. There are a variety of calcium and magnesium salts that are suitable for human consumption and are suitable for contributing to bone growth according to the invention. Suitable calcium salts include, but are not limited to, calcium lactate and calcium gluconate. Suitable magnesium salts include, but are not limited to, magnesium glycerophosphate and magnesium sulfate. Magnesium glycerophosphate is a desired choice of the magnesium salt because magnesium glycerophosphate also contributes a phosphorous component to the composition. Phosphorous is believed to contribute to bone density and a healthy skeletal system.

Isoflavones are a dietary source for increasing bone density. The isoflavones suitable for the invention include, but are not limited to, the naturally occurring soy isoflavones from soy including the classes such as daidzein, genistein, and glycitein in a variety of forms (e.g., glycosidic and acetylated forms). Soy isoflavones are commercially available, for example, from Archer Daniels Midland of Decatur, Ill. Synthetically derived isoflavones may also be suitable.

Oligosaccharides include, but are not limited to, fructo-oligosaccharides and gluco-oligosaccharides. Inulin, a fructo-oligosaccharide is derived principally from chickory root. Oligosaccharides such as inulin provide at least two benefits. First, oligosaccharides increase the intestinal absorption of minerals, such as calcium and magnesium. Second, oligosaccharides improve the intestinal microflora by increasing the amount of colonic bifidobacteria. Inulin as an oligosaccharide source is commercially available, for example, from Imperial Suiker Unier of Sugar Land, Tex.

Vitamin $D_3$ stimulates intestinal absorption of minerals, particularly calcium, and calcium mobilization. Cold water soluble (CWS) Vitamin $D_3$ (cholecalciferol) is available commercially as from BASF Corporation of Paramus, N.J., or Hoffmann-La Roche of Nutley, N.J.

In addition to the above components, the composition of the invention may also include, but is not limited to, additional minerals such as phosphorous and zinc. Phosphorous, as noted above, promotes bone density. Zinc may be added, in particular, to offset any impact on zinc absorption caused by calcium uptake. Vitamins including Vitamin C (ascorbic acid) and Vitamin K (phylloquinone) may also be added to the composition of the invention. Vitamin C helps utilize the absorbed calcium and maintains normal calcium crystals in bones. Vitamin K is believed to reduce the urinary excretion of calcium and the production of bone resorbing agents such as prostaglandin E2 or interleukin 6. Additional components such as stabilizing agents, acidifiers, and sweeteners may further be added.

The composition of the invention can take many forms. These forms include, a ready-to-drink beverage of a portion, including the entire portion, of the predetermined requirements (e.g., predetermined daily requirements) for maximizing the intake and utilization of bone building (e.g., bone density promoting) materials such as calcium, magnesium, and isoflavone. The invention may also take the form of a beverage preparation of, for example, a dry mix or a concentrate syrup to be mixed with a liquid such as water, milk, or juice. In this manner, a more concentrated form of the composition of the invention may be packaged to be diluted with a liquid. Still further, the composition of the invention may take the form of a paste that may be spread on a wafer such as a sweet wafer (e.g., cookie) or a cracker. Yet further, a composition of the invention may be encompassed in the form of a bar. It is to be appreciated that in these other forms (e.g., paste, bar, etc.), the invention may constitute the entire portion of a predetermined amount (e.g., predetermined daily amount) of the components or a smaller portion of such predetermined amount. Still further, it should be appreciated that other forms of the composition may be contemplated without deviating from the spirit and scope of the invention. For example, dietary forms such as cereals or candies may also be utilized.

In one embodiment, the composition is a beverage comprising the entire portion or a smaller portion of the daily predetermined quantity of the desired components of the composition for increasing bone density and/or reducing the risk of osteoporosis.

In particular, the composition of a beverage comprises, in one example, a portion of the individual components corresponding to a predetermined daily amount dosage recommending eight servings per day. In this example, eight servings are chosen with the objective that an ordinary person will take around eight 240 mL dosages daily.

Table 1 represents a suitable range of the daily amount of individual components of the composition of the invention.

TABLE 1

| Predetermined Daily Amounts | |
| --- | --- |
| Calcium | 500–2000 mg |
| Magnesium | 100–700 mg |
| Isoflavones (soy) | 50–200 mg |
| Inulin | 5–20 g |
| Vitamin D3 | 400–800 IU (1 IU = 0.025 µg) |
| Vitamin K | 35–85 µg |
| Vitamin C | 200–1000 mg |
| Zinc | 4–30 mg |

In one embodiment, the composition as a beverage includes a stabilizing agent to facilitate the solubilization of the individual components in solution. The stabilizing agent is one or more of a maltol commercially available from Cultor Food Science, Inc. of Ardsley, N.Y. A composition of carrageenan and maltodextrin such as sold under the trademark INSTA*THICK C-15L™ by Zumbro Inc. of Hayfield, Minn., or a xanthan gum such as sold under the trademark KELTROL™, by NutraSweet Kelco Company of Deerfield, Ill. Preferably, a composition is combined with a combination of maltol and a composition of carrageenan and maltodextrin or a composition of maltol and xanthan gum(s). In this manner, the solubility of the individual components of the composition, particularly soy isoflavones, is improved. A suitable range of maltol in the beverage composition of the invention is 0.1 g to 0.4 g for a 240 mL composition. The level of 0.1 g in 240 mL aqueous solution was found to increase the solubility of soy isoflavones in aqueous solution. A suitable range of a composition of carrageenan and maltodextrin commercially available under the trademark INSTA*THICK is 1.0 g to 4.0 g for a 240 mL composition. The level of 1 g in 240 mL water was found to increase the solubility of soy isoflavones in aqueous solution. A suitable range of xanthan gum commercially available under the trademark KELTROL-T is 0.024 g to 0.096 g for a 240 mL composition. The level of 0.024 g in 240 mL aqueous solution generally does not create a viscous mouthfeel. The 0.096 usage level is used in the preparation of 4x concentrated syrup.

Table 2 shows the combination of maltol and INSTA*THICK C-15L™ increases the solubility of three soy isoflavones, particularly genistin (>75%), in aqueous solution as assayed by high performance liquid chromatography. Microfiltration through a membrane with pore size from 0.45 to 1.2 µm resulted in clarified solutions with less precipitation compared with non-microfiltered ones as shown in Table 3.

TABLE 2

Comparison of percent recovery of three soy isoflavones in the filtrate with and without maltol and/or INSTA*THICK C-15L ™.

| Soy Isoflavone | % Recovery No additives | % Recovery with maltol | % Recovery with INSTA* THICK C-15L ™ | % Recovery with maltol and INSTA* THICK C-15L ™ |
| --- | --- | --- | --- | --- |
| Daidzin | 93.26% | 98.70% | 98.94% | 97.64% |
| Glycitin | 96.60% | 99.23% | 101.04% | 98.75% |
| Genistin | 59.07% | 77.77% | 76.69% | 74.28% |

TABLE 3

Comparison of turbidity of filtered and nonfiltered samples measured by turbidimetry using spectrophotometer.

| Samples | Absorption at 457 nm |
|---|---|
| Microfiltration through glass fiber membrane with a pore size of 0.7 µm | 0.160 |
| Non-microfiltration | 0.125 |

Different levels of sweeteners (such as, but not limited to, sugars, sugar alcohols, monosaccharides, disaccharides, trisaccharides) and different flavors may be used in the beverage product. The composition can be formed as a low calorie composition with artificial sweeteners such as, but not limited to, ASPARTAME™, ACESULFAME-K™, SACCHARIN™, or SUCRALOSE™ or any combination of the above. Appropriate flavors include, but are not limited to, orange, peach, cranberry, tangerine, raspberry, grapefruit, mango, black cherry, strawberry, or any combination of the above flavors. The beverage may be clear, colorless, translucent, and/or contain a colorant. Suitable colorants can be from natural sources or from certified F&DC colorants.

In one embodiment, the flavor characteristics are selected for optimum compatibility with other ingredients, particularly inulin, soy isoflavone, vitamins and minerals, to achieve a superior taste profile.

The composition, in one embodiment, is adjusted to be at a pH less than 7, and preferably between 3 and 7, and more preferably between 4 and 5. The addition of an acidifier such as a combination of malic acid and citric acid to one embodiment of the composition is utilized to adjust the pH from about 4 to about 7 (preferably below 4.6) and to overcome precipitation problems associated with prior art compositions. The pH of the beverage product between 4 and 5 is suitable because inulin is stable in solution above pH 4 at room temperature. Also, this medium-high acid (i.e., pH<4.6) of the beverage is desirable for bacterial control.

A preferred approximate ratio of calcium compound, magnesium compound, soy isoflavones, and the oligosaccharide inulin relative to one another is shown in Table 4.

TABLE 4

Ratio of components in a composition

| Components | Ratio |
|---|---|
| Ca:Mg | 5:1 to 3:1 |
| Ca:soy isoflavones | 10:1 |
| Ca:inulin | 1:10 |
| Mg:soy isoflavones | 2:1 to 3:1 |
| Mg:inulin | 1:50 to 1:30 |
| Soy isoflavones:inulin | 1:100 |
| Zinc | 4–30 mg |

Representative compositions of suitable beverages are provided. In the following ranges, the lower value represents a 240 mL composition containing one-eighth of a preferred predetermined dosage level and the upper value is a 4× concentrate of a preferred predetermined dosage level comprises:

(a) about 0.26 to 8.33% (w/v) of inulin in a soluble form;
(b) about 0.0052 to 0.166 ppm (w/v) of Vitamin $D_3$ as cholecalciferol;
(c) about 0.0026 to 0.083% (w/v) of soy isoflavones from concentrated extracts;
(d) about 0.026 to 0.83% (w/v) of calcium in a biologically acceptable soluble calcium salts, preferably calcium lactate;
(e) about 0.0052 to 0.166% (w/v) of magnesium in a biologically acceptable soluble magnesium salts, preferably magnesium glycerophosphate;
(f) about 2.08 ppm to 66.67 ppm (w/v) of zinc in a biologically acceptable soluble zinc salts, preferably zinc citrate;
(g) about 0.018 ppm to 0.58 ppm (w/v) of Vitamin K blend (1% phylloquinone);
(h) about 0.01 to 0.417% (w/v) of ascorbic acid;
(i) about 0.0052 to 0.166% (w/v) of maltol and 0.052 to 1.67% (w/v) of Insta*Thick C-15L (containing carrageenan and maltodextrin) from Zumbro Inc., or about 0.0052 to 0.166% (w/v) of maltol and about 12.5 ppm to 400 ppm (w/v) of xanthan gums;

The following examples describe methods for preparing a beverage composition of the invention as a single strength (comprising, in this example, the daily predetermined amounts of the individual components) or as a beverage preparation in the form of a concentrate syrup (3× to 4× the daily predetermined amount).

METHOD 1

SINGLE STRENGTH FORMULA (To make 960 mL=4× 240 mL servings)

1. Heat approximately 180 mL deionized water to about 80 to 85 C.
2. Add 0.4g maltol to the hot water and stir until it is completely dissolved.
3. Add 4 g INSTA*THICK C-15L™ to the above mixture and stir until it is completely dispersed.
4. Add 500 mg soy isoflavone extract to the above mixture and stir at 80 to 85 C. for at least 10 minutes.
5. Filter the hot solution through 1.2 µm glass fiber filter. Rinse the container with about 2×200 mL deionized water and filter the rinse through the same filter too.
6. To the above hot filtrate, add sequentially 14.28 g calcium lactate pentahydrate, 3.76 g magnesium glycerophosphate, 0.0532 g zinc citrate dihydrate, 1.344 g citric acid, 0.688 g malic acid, 0.0232 g sodium citrate dihyrate, and a premix of 25 g sugar and 22.6 g inulin. Stir until no particulate remains. Then add 75 g sugar and stir until it is completely dissolved.
7. Cool the mixture to room temperature, add 2.5 g ascorbic acid, 0.0536 g Vitamin $D_3$ and 0.042 g Vitamin K blend (1% phylloquinone). Stir until the solids are dissolved.
8. Add optional flavors and colorants.
9. Adjust the volume to 960 mL with deionized water.
10. Divide the volume into four 240 mL parts for serving size.

METHOD 2 (with Xanthan gum)

SINGLE STRENGTH FORMULA (To make 960 mL=4× 240 mL serving)

1. Heat approximately 400 mL deionized water in a container to about 80 to 85 C.
2. Add 0.4 g maltol to the hot water and stir until it is completely dissolved.
3. Add 0.5 g of soy isoflavone extract to the above mixture and stir under 80 to 85 C. until the mixture is clear.
4. While hot, filter the mixture through a 1.2 µm glass fiber filter. Rinse the container with about 2×40 mL deionized water and filter the rinse through the same filter.
5. To above filtrate, add sequentially 14.28 g calcium lactate pentahydrate, 3.76 g magnesium glycerophoshate, 0.0532 g zinc citrate dihydrate, 1.344 g citric acid, 0.688 g malic acid, 0.0232 g sodium citrate dihydrate granular, a premix of 100 g to 113.12 g sugar (depending on flavor) and 22.6 g inulin. In order to achieve the astrigency/tartness associated with some flavors' character, the following ingredients have been added: 0.0308 g of tartaric acid in pink grapefruit; 0.03 g of fumaric acid in cranberry-raspberry; and 0.308 g of fumaric acid and 0.24 g of sodium citrate dihydrate granular in raspberry. Stir the contents until all solids are completely dissolved.

6. Cool the mixture to room temperature, and add 2.5 g ascorbic acid, 0.0536 g Vitamin $D_3$, and 0.0424 g Vitamin K blend (1% phylloquinone).
7. Stir until solids are dissolved.
8. In high shear, disperse 0.096 g xanthan gums (KELTROL-T™) in about 40 mL hot deionized water at about 60° C. Cool the solution to room temperature.
9. Add the xanthan gum solution to step 6 above and mix well.
10. Add optional flavors and colorants.
11. Adjust the volume to 960 mL with deionized water.
12. Divide the volume into four 240 mL parts for serving size.

METHOD 3
CONCENTRATED SYRUP (4×) PREDETERMINED DOSAGE PREPARATION (Diluted 1 part syrup to 3 parts water to make a single strength)

(1) Prepare a mixture of maltol, Insta*Thick C-15L, soy isoflavone extract, calcium salts, magnesium salts, zinc salts, and fruit acids in water at about 80 to 85° C.;
(2) While hot, filter the dispersion of (1) through a 1.2 µm glass fiber filter and then cool down the filtrate to about 50° C.;
(3) Add a premix of inulin and sugar to the filtrate of (2) and cool the dispersion to room temperature;
(4) Add to the mixture of (3) vitamins, flavors, colorants and optional ingredients dissolved in water; all the said ingredients are added with agitation.

The beverage composition of the invention can be pasteurized through tunnel pasteurization or hot-fill techniques as known in the art. A high temperature/short time condition is desirable for retaining maximum product quality. Alternatively, the beverage composition can be prepared with cold-fill techniques in conjunction with preservation by the addition of preservatives including, but not limited to, potassium benzoate and potassium sorbate. Carbonation may also be performed to any desired volume, with an antifoaming agent such as AF emulsion (30% polydimethylsiloxane).

The above description related to forming the composition of the invention in the form of a beverage. With this description in mind, it is to be appreciated that conventional food processing techniques may be employed to prepare other forms of the composition, including powders, pastes, and bars.

The composition of the invention provides the necessary nutrients for preventing osteoporosis and also includes the principal components for enhancing bioavailability and metabolism of those nutrients. The principal components to improve bone density are believed to be calcium, magnesium, phosphorus, Vitamin D, Vitamin K, and isoflavones. It is believed that the composition of the invention gives better results than have heretofore been observed in prior art teachings.

Example 1

Formula for Orange Peach Flavored Beverage

| INGREDIENT | AMOUNT, g (per 240 mL serving) |
|---|---|
| Inulin | 5.65 |
| Sugar | 25.0 |
| Calcium lactate, pentahydrate | 3.57 |
| Magnesium glycerophosphate | 0.94 |
| Zinc citrate, dihydrate (30%) | 0.0133 |
| Citric acid | 0.336 |
| Malic acid | 0.172 |
| Sodium citrate, dihydrate granular | 0.0058 |
| Ascorbic acid | 0.625 |
| Vitamin $D_3$ (0.25%) | 0.0134 |
| Vitamin K, 1% phylloquinone | 0.0105 |
| Soy isoflavones (40 to 50% concentrate) | 0.1 to 0.125 |
| Maltol | 0.10 |
| INSTA*THICK C-15L ™ | 1.0 |
| Natural orange flavor | 0.4056 |
| Natural peach flavor | 0.312 |
| Natural red colorant, cochineal extract | 0.048 |
| Natural orange emulsion colorant | 0.012 |

Example 2

Formula for Pink Grapefruit Flavored Beverage

| INGREDIENT | AMOUNT, g (per 240 mL serving) |
|---|---|
| Inulin | 5.65 |
| Sugar | 25.5 |
| Calcium lactate, pentahydrate | 3.57 |
| Magnesium glycerophosphate | 0.94 |
| Zinc citrate, dihydrate (30%) | 0.0133 |
| Citric acid | 0.336 |
| Malic acid | 0.172 |
| Tartaric acid | 0.0077 |
| Sodium citrate, dihydrate granular | 0.0058 |
| Ascorbic acid | 0.625 |
| Vitamin $D_3$ (0.25%) | 0.0134 |
| Vitamin K, 1% phyiloquinone | 0.0105 |
| Soy isoflavones (40 to 50% concentrate) | 0.1 to 0.125 |
| Maltol | 0.10 |
| INSTA*THICK C-15L ™ | 1.0 |
| Natural pink grapefruit flavor | 0.3631 |
| Natural red colorant, cochineal extract | 0.0503 |

Example 3

Formula for Citrus Berry Flavored Beverage

| INGREDIENT | AMOUNT, g (per 240 mL serving) |
|---|---|
| Inulin | 5.65 |
| Sugar | 25.0 |
| Calcium lactate, pentahydrate | 3.57 |
| Magnesium glycerophosphate | 0.94 |
| Zinc citrate, dihydrate (30%) | 0.0133 |
| Citric acid | 0.336 |
| Malic acid | 0.172 |
| Sodium citrate, dihydrate granular | 0.0198 |
| Ascorbic acid | 0.625 |
| Vitamin $D_3$, CWS (0.25%) | 0.0134 |
| Vitamin K, 1% phylloquinone | 0.0105 |
| Soy isoflavones (40 to 50% concentrate) | 0.1 to 0.125 |

-continued

Formula for Citrus Berry Flavored Beverage

| INGREDIENT | AMOUNT, g (per 240 mL serving) |
|---|---|
| Maltol | 0.1 |
| INSTA*THICK C-15L ™ | 1.0 |
| Natural raspberry flavor | 0.24 |
| Natural Tangerine-Orange flavor | 0.156 |
| Cochineal extract | 0.0499 |
| Beta carotene 2% water dispersion | 0.013 |

Example 4

Formula for Raspberry Flavored Beverage

| INGREDIENT | AMOUNT, g (per 240 mL serving) |
|---|---|
| Inulin | 5.65 |
| Sugar | 25.5 |
| Calcium lactate, pentahydrate | 3.57 |
| Magnesium glycerophosphate | 0.94 |
| Zinc citrate, dihydrate (30%) | 0.0133 |
| Citric acid | 0.336 |
| Malic acid | 0.172 |
| Fumaric acid | 0.0077 |
| Sodium citrate, dihydrate | 0.0658 |
| Ascorbic acid | 0.625 |
| Vitamin $D_3$, CWS (0.25%) | 0.0134 |
| Vitamin K, 1% phylloquinone | 0.0105 |
| Soy isoflavones (40 to 50% concentrate) | 0.1 to 0.125 |
| Maltol | 0.1 |
| INSTA*THICK C-15L ™ | 1.0 |
| Natural raspberry flavor | 0.312 |
| Cochineal extract | 0.24 |

Example 5

Formula for Cranberry Raspberry Flavored Beverage

| INGREDIENT | AMOUNT, g (per 240 inL serving) |
|---|---|
| Inulin | 5.65 |
| Sugar | 25.0 |
| Calcium lactate, pentahydrate | 3.57 |
| Magnesium glycerophosphate | 0.94 |
| Zinc citrate, dihydrate (30%) | 0.0133 |
| Citric acid | 0.336 |
| Malic acid | 0.172 |
| Fumaric acid | 0.0075 |
| Sodium citrate, dihydrate | 0.0058 |
| Ascorbic acid | 0.625 |
| Vitamin $D_3$, CWS (0.25%)* | 0.0134 |
| Vitamin K, 1% phylloquinone | 0.0105 |
| Soy isoflavones (40 to 50% concentrate) | 0.1 to 0.125 |
| Maltol | 0.1 |
| INSTA*THICK C-15L ™ | 1.0 |
| Natural cranberry flavor | 0.2086 |
| Natural raspberry flavor | 0.0751 |
| Cochineal extract | 0.36 |

Example 6

Formula for Citrus Blend Flavored Beverage

| INGREDIENT | AMOUNT, g (per 240 mL serving) |
|---|---|
| Inulin | 5.65 |
| Sugar | 25.0 |
| Calcium lactate, pentahydrate | 3.57 |
| Magnesium, glycerophosphate | 0.94 |
| Zinc citrate, dihydrate (30%) | 0.0133 |
| Citric acid | 0.336 |
| Malic acid | 0.172 |
| Sodium citrate, dihydrate | 0.0058 |
| Ascorbic acid | 0.625 |
| Vitamin $D_3$, CWS (0.25%) | 0.0134 |
| Vitamin K, 1% phylloquinone | 0.0105 |
| Soy isoflavones (40 to 50% concentrate) | 0.1 to 0.125 |
| Maltol | 0.1 |
| INSTA*THICK C-15L ™ | 1.0 |
| Natural pink grapefruit flavor | 0.1728 |
| Natural orange flavor | 0.2074 |
| Natural lemon flavor | 0.3110 |
| Beta carotene | 0.2208 |

Example 7

Formula for Lemon Lime Flavored Beverage

| INGREDIENT | AMOUNT, g (per 240 mL serving) |
|---|---|
| Inulin | 5.65 |
| Sugar | 25.5 |
| Calcium lactate, pentahydrate | 3.57 |
| Magnesium glycerophosphate | 0.94 |
| Zinc citrate, dihydrate (30%) | 0.0133 |
| Citric acid | 0.336 |
| Malic acid | 0.172 |
| Fumaric acid | 0.03 |
| Sodium citrate, dihydrate | 0.0058 |
| Ascorbic acid | 0.625 |
| Vitamin $D_3$, CWS (0.25%) | 0.0134 |
| Vitamin K, 1% phylloquinone | 0.0105 |
| Soy isoflavones (40 to 50% concentrate) | 0.1 to 0.125 |
| Maltol | 0.1 |
| INSTA*THICK C-15L ™ | 1.0 |
| Natural lemon-lime flavor | 0.720 |
| Beta carotene 2% water dispersion | 0.01 |

In the preceding detailed description, the invention is described with reference to specific embodiments thereof. It will, however, be evident that various modifications and changes may be made thereto without departing from the broader spirit and scope of the invention as set forth in the claims. The specification and drawings are, accordingly, to be regarded in an illustrative rather than a restrictive sense.

What is claimed is:

1. A method comprising:
   administering a beverage composition suitable for human consumption comprising effective amounts of the following solubilized components:
   a calcium compound;
   an organic acid in an amount up to the equivalent amount of a calcium of the calcium compound;
   an isoflavone; and
   inulin,
   wherein the effective amounts are sufficient to reduce the risk of bone density loss and are solubilized by a stabilizing agent comprising one or more of maltol, carrageenan and maltodextrin, and xanthan gum.

2. The method of claim 1, wherein the composition further comprises amounts of Vitamin $D_3$ and Vitamin K.

3. The method of claim 2, wherein the stabilizing agent comprises maltol and one of carrageenan and maltodextrin and a xanthan gum, the stabilizing agent present in an amount such that the solubility of the soy isoflavone in the beverage is greater than 75 percent.

4. The method of claim 3, wherein the effective amounts of the individual components in the composition are selected for an individual serving size representing a portion less than a daily amount.

5. The method of claim 1, wherein the composition further comprises effective amounts of a magnesium compound.

6. A method comprising:

administering a beverage composition suitable for human composition comprising amounts of the following solubilized compounds:

a calcium compound;

a magnesium compound;

an organic acid in an amount up to the equivalent amount of a calcium of the calcium compound;

an isoflavone; and fructo-oligosaccharide, wherein the effective amounts are sufficient to reduce the risk of bone density loss and are solubiized by a stabilizing agent comprising one or more of maltol, carrageenan and maltodextrin, and xanthan gum.

7. The method of claim 6, wherein the composition further comprises Vitamin $D_3$.

8. The method of claim 6, wherein the stabilizing agent comprises maltol and one of carrageenan and maltodextrin and a xantham gum, the stabilizing agent present in an amount such that the solubility of the soy isoflavone in the beverage is greater than 75 percent.

9. The method of claim 6, wherein the effective amounts of the individual components in the composition are selected for an individual serving size representing a portion less than a daily amount.

* * * * *

UNITED STATES PATENT AND TRADEMARK OFFICE
CERTIFICATE OF CORRECTION

PATENT NO. : 6,436,446 B1
DATED : August 20, 2003
INVENTOR(S) : Forusz et al.

It is certified that error appears in the above-identified patent and that said Letters Patent is hereby corrected as shown below:

Title page,
Item [56], References Cited, OTHER PUBLICATIONS, "Hideo Tomamatsu" reference, please delete "RAFTLINE" and insert -- RAFTILINE --; and please delete "RAFTILOS" and insert -- RAFTILOSE --; and please delete "Abortion" and insert -- Absorption --.

Signed and Sealed this

Thirteenth Day of July, 2004

JON W. DUDAS
*Acting Director of the United States Patent and Trademark Office*